United States Patent [19]

Ward

[11] 3,933,780
[45] Jan. 20, 1976

[54] HIGH SOLIDS SOAPS OF FATTY ACIDS AND FATTY OIL DERIVED POLYCARBOXYLIC ACIDS

[75] Inventor: Benjamin F. Ward, Charleston, S.C.

[73] Assignee: Westvaco Corporation, New York, N.Y.

[22] Filed: May 21, 1973

[21] Appl. No.: 361,939

[52] U.S. Cl............................ 260/97.5; 260/18 R
[51] Int. Cl.² ........................................ C09F 1/04
[58] Field of Search..... 260/97.5, 22 R, 23 R, 18 R; 162/179, 22 T

[56] References Cited
UNITED STATES PATENTS

| | | | |
|---|---|---|---|
| 2,994,635 | 8/1961 | Reaville | 260/97.5 |
| 3,257,377 | 6/1966 | Hannah | 260/97.5 |
| 3,639,650 | 2/1972 | Cummings | 260/18 R |

*Primary Examiner*—M. J. Welsh
*Attorney, Agent, or Firm*—Richard L. Schmalz; Ernest B. Lipscomb, III

[57] ABSTRACT

Disclosed herein are high solids content liquid polycarboxylic acid soaps made from long chain fatty acids and fatty oils by reaction with a maleinizing agent. This addition reaction is performed at a temperature between 180°C. and 300°C. preferably 190°C. and 220°C., between fatty acids and fatty oils from soya oil, tallow, corn oil, linseed oil, sunflower oil, tung oil, and tall oil fatty acids with maleyl compounds such as maleic anhydride. These addition reaction products when converted to soaps, such as potassium, sodium and ammonium, have a solubility uniquely above that noted before. The invention also includes mixtures of blends of the polycarboxylic acids with fatty acids and oils.

1 Claim, No Drawings

3,933,780

HIGH SOLIDS SOAPS OF FATTY ACIDS AND FATTY OIL DERIVED POLYCARBOXYLIC ACIDS

BACKGROUND OF THE INVENTION

1. Field of the Invention

This invention relates to high solids polycarboxylic acid soap compositions. More particularly, this invention relates to soap compositions having increased carboxyl content thereby having an increased soap solubility or solids content. These high solids soaps are the addition reaction of unsaturated, conjugated and unconjugated fatty acids and a maleyl compound.

2. The Prior Art

Two considerations which are important to fatty acid soap users are the saponifying agent used for the soap and the level of solids obtainable in maintaining a fluid soap. It seems in the majority of cases these two are related, for of the common saponifying agents, potassium and sodium the potassium soap is much more soluble. Therefore, when relatively high solids soaps are desired, the potassium soap is the standard for fatty acids. In most cases the sodium soap would serve just as well and be cheaper to produce, but since it is much less soluble and tends to crystallize, it is normally avoided. For example, using potassium soaps, the highest solids soaps that are still fluid at room temperature for several short and long chain fatty acid soaps are as follows:

| | |
|---|---|
| Caprylic ($C_8$) | 45% |
| Capric ($C_{10}$) | 40% |
| Lauric ($C_{12}$) | 35% |
| Coconut (Mixture of $C_{10}$, $C_{12}$, $C_{14}$) | 36% |
| Tallow ($C_{18}$) | 17% |
| Oleic ($C_{18}$) | 20% |
| Dimer Acid ($C_{36}$) | 23% |

As is obvious, the shorter chain soaps are more soluble and fluid than oleic-type fatty acid. The same trend is apparent with the sodium soaps of the various acids except the solubilities are lower.

The high solid soaps are made as adducts of the Diels-Alder reaction, using maleyl compounds as the dienophiles or by an addition reaction. The literature is therefore full of patents extolling the benefits and utility derived from the reaction of maleic anhydride with rosin, with rosin-fatty acid mixtures, fatty acids, and with many naturally occurring oils; however, none specifically teach increased solubility of soaps. In this regard, U.S. Pat. No. 3,639,650 to L. O. Cummings discloses adducts of unsaturated, unconjugated fatty oil, such as glyceride, and a maleyl compound reacted at a temperature between 300°F. (149°C.) and 350°F. (177°C.) in the presence of sulfur dioxide to reduce color for use in coatings. In The Journal of the American Oil Chemists' Society, (Volume 34, page 136 (1957)), Danzig et al. teach in an article entitled "Reactions of Conjugated Fatty Acids, V. Preparation and Properties of Diels-Alder Adducts and Their Esters from Trans, Trans-Conjugated Fatty Acids Derived From Soybean Oil" using iodine to convert linoleic portions of soybean fatty acids to the trans, trans conjugated form to prepare cyclic adducts.

It has been found that high solid polycarboxylic acid soaps may be made to substantially lessen the problem of gelation and extend crystallization of fatty acid soaps to before unknown high solids content without a conversion catalyst. It is therefore the general object of this invention to provide polycarboxylic acid soap compositions that are water soluble at high soap solids content. Another object is to provide a polycarboxylic acid soap using a variety of neutralizing agents and still retaining high water solubility. Still another object of this invention is to provide a process for making the high solids content polycarboxylic acid soaps from a variety of fatty acid and fatty oils. An even further object of this invention is to provide maleyl modified fatty acids and oils having a saponification number from 200 to 400 and lower viscosity at a given solids level than the unmodified fatty acid or oil.

Other objects, features and advantages of this invention will become apparent from the following detailed description.

SUMMARY OF THE INVENTION

This invention is directed to high solids content liquid soaps made from long chain fatty acids and fatty oils by reaction with a maleinizing agent. Further the invention includes blends of the polycarboxylic acid soaps and the soaps of fatty acids or fatty oils. The high solids polycarboxylic acid soaps are the potassium, sodium or ammonium soaps of the addition reaction of a fatty acids, such as tall oil fatty acid, soya fatty acid, corn, cottonseed and tallow fatty acid, or a fatty oil, such as soya oil, corn oil, linseed oil, cottonseed oil, sunflower oil and tung oil with a maleyl compound such as maleic anhydride. The fatty acid or fatty oil and maleyl compound are heated from between 180°C. and 300°C., preferably 190°C. to 200°C. for from 30 minutes to six hours to effect the reaction. The blends of polycarboxylic acid soaps and soaps of fatty acids or oils ranges from 90 to 10 percent to 10 – 90 percent by solids weight.

DETAILED DESCRIPTION OF THE INVENTION

The essence of this invention is the discovery that polycarboxylic acids made from fatty acids containing some unsaturated isomers when converted into their potassium soaps provide not only the advantages of conventional soaps, but also provide the additional advantage of increased water solubility, a notable freedom from liquid crystal formation and lower viscosity than the unmodified compound. The process includes heating an admixture of such reactants at a temperature between 180°C. and 300°C., preferably 190°C. to 220°C. for at least 30 minutes to six hours to obtain a saponification number between 200 and 500, preferably 210 to 250.

The fatty oils useful in the present invention include safflower oil, soya oil, sunflower oil, cotton seed oil, linseed oil, corn oil, and tung oil. Equally as useful are tall oil fatty acids, soya fatty acids and tallow fatty acids, as well as, other long chain fatty acids from any source containing even a minor fraction of unsaturated acids. The term long chain fatty acid used herein include any such acid having at least 10 carbon atoms in the chain and suitably from 10 to 26 carbon atoms. A description of the composition of individual fatty acids present in some fatty acids and fatty oils is shown in Table I.

The maleyl compound is preferably maleic anhydride. Other maleyl compounds are useful herein, such as maleic acid which changes to maleic anhydride when heated to about 130°C. since maleic anhydride is readily available and is relatively inexpensive, the invention will be described with reference to this compound. The starting mixture may incorporate a stoichiometric amount of the anhydride with respect to the amount the fatty oil or fatty acid to be reacted, but more or less can be employed if desired. Evidence indicates that substantially less than the stoichiometric amount of maleic anhydride give adequate increases in solubility. In general, there is admixed from about 10 to about 35 percent by weight, based on the total weight of two reactants, of the maleyl compound, expressed as maleic anhydride though a range of 1 to 40 percent is practical.

percent solids having a viscosity below 140 centipoise at 25°C.

Similar beneficial results were obtained when a spectrum of commercially vailable fatty acids and oils are maleinized in a similar manner. As shown in Example 2, all except corn oil give potassium soap solubilities in excess of 44 percent at 100 centipoise viscosity. Maleic treatment of linseed oil gives the highes soap solubility (52 percent at 100 centipoise and this oil was not treated at the maximum theoretical reactivity level). Tallow fatty acids, which have little polyunsaturated acid, give a remarkably soluble product. Soaps with

TABLE 1

GLC ANALYSES OF FATTY ACIDS AND OILS

| Individual Fatty Acid | Chain Length Carbons | Double Bonds | Tall Oil Fatty Acid | Soya Fatty Acid | Tallow Fatty Acid | Corn Oil | Linseed Oil | Tung Oil | Coconut Fatty Acid |
|---|---|---|---|---|---|---|---|---|---|
| $C_{8-10}$ | 10 | 0 | — | — | — | — | — | — | 13.0 |
| Lauric | 12 | 0 | — | T | 0.6 | — | — | — | 49.5 |
| Myristic | 14 | 0 | — | 1.2 | 3.5 | — | — | — | 19.5 |
| Myristoleic | 14 | 1 | — | — | 0.8 | 0.5 | — | — | — |
| Palmitic | 16 | 0 | 2.8 | 10.8 | 26.3 | 12.4 | 6.0 | 4.0 | 8.5 |
| Palmitoleic | 16 | 1 | 0.8 | 2.1 | 4.9 | 0.7 | — | — | — |
| Stearic | 18 | 0 | 2.1 | 0.6 | 17.5 | 1.8 | 3.5 | 1.0 | 2.0 |
| Oleic | 18 | 1 | 46.3 | 33.3 | 40.2 | 24.7 | 20.0 | 8.5 | 6.0 |
| Linoleic | 18 | 2 | 40.1 | 50.2 | 3.6 | 59.0 | 14.5 | 3.5 | 1.5 |
| Linolenic | 18 | 3 | — | — | — | — | 56.0 | 3.0 | — |
| Elaeostearic | 18 | 3 | — | — | — | — | — | 80.0 | — |
| Other | — | — | 7.9 | 1.8 | 2.6 | 0.9 | — | — | — |
| % Unsaturated Acids | | | 87.2 | 85.6 | 49.5 | 84.9 | 90.5 | 95.0 | 7.5 |
| Average Carbon Chain Length of Fatty Acids | | | 18.0 | 17.8 | 17.3 | 17.8 | 17.9 | 17.3 | 12.9 |

In general, no catalyst is needed to perform this addition reaction as the maleyl compounds easily undergo reaction with the double bonds within the stated temperature range. Maleic anhydride, in addition to forming ring adduct with conjugated fatty acids, forms an addition reaction with any single double bond. This results in the addition of a branch with at least two carboxyls. Linoleic acid can thus add two moles of maleic anhydride either through a combination of Diels-Alder reaction plus addition reaction if it is in the conjugated form or through the addition of two moles of maleic by the addition reaction if it is non-conjugated. Oleic acid, which cannot react with acrylic acid in the Diels-Alder reaction could be di-carboxylated with maleic anhydride by way of the addition reaction. Linoleic and oleic acid could in this way become penta and tri-carboxylic acids respectively. Linoleic could add three moles of maleic and theoretically yields a septacarboxylic acid.

Maleic anhydride reaction products of various commercially important fatty acid mixtures and oils were used as starting materials. Conventional $C_{18}$ fatty acids have limited solubility even as potassium soaps. Further, only a 1.5 percent solids difference exists at 100 centipoise between tallow fatty acid and soya soaps. The viscosity of all increase drastically on further increases in colids accompanied by the formation of liquid crystals. If high solids soap solutions are required, it is now necessary to use the more expensive shorter chain acids, such as coconut fatty acids. These coconut fatty aicd soaps reach 100 centipoise viscosity at 37.5% potassium soap solids versus 20.6% for tallow and tall oil fatty acid and 19.0% for soya fatty acid soap. Increases in solubility are obtained from polycarboxylation of tall oils fatty acids with maleic anhydride, as for example, the potassium soaps are soluble at 45 solubility properties identical to coconut soaps are made by either blending tallow fatty acid into the modified tallow fatty acids or by proper choice of the level of maleic modification. The commercially important 75/25: tallow/coconut blend is thus simulated in potassium soap solubility by either reacting tallow fatty acids with 4.1 parts maleic anhydride per 100 of fatty acids or by a 81.9/18.1 blend of tallow fatty acids and modified tallow fatty acid. Apparently, for maximum soap solubility, a mixture of Diels-Alder and addition products give optimum results. An infinite variety of products can thus be made by proper choice of fatty acid or fatty oil to be modified, the level of modification with maleyl compound, and choice of fatty acid used for blending. The blending of polycarboxylic acid soaps and unmodified fatty acids may be practically accomplished at a ratio of 90 to 10 percent by weight polycarboxylic acid to 10 to 90 percent by weight unmodified fatty acid.

One particularly interesting and useful aspect of these maleinized products is that they exhibit the solubility characteristics of much shorter chain fatty acids, especially in admixtures. Factors which reduce the viscosity and liquid crystal formation tendency of conventional monocarboxylic fatty acid soaps are: (1) reduction in average chain length; (2) increase in polydispersity of chain length or unsaturation; (3) increase in hydration conferred by proper choice of alkali; (4) introduction of shape factors such as rings or side chains; and (5) increase in polarity and hydration with additional carboxyls. If soaps of two different monocarboxylic fatty acids of similar chain length and unsaturation are mixed, one expects and does get linear blending with respect to viscosity. Thus a tall oil potassium soap and a soya potassium soap, both at 100 centipoise viscosity would yield 100 centipoise viscosity mixtures at any blend ratio. Where a small difference exists, such as when tallow ($C_{average} = 17.3$, 50% saturated, mild dispersion of molecular weight) is mixed with soya ($C_{average}$ = 17.8, 15% saturated, small dispersion of molecular weight), we would expect a little nonlinearity. Where the difference is great, such as with coconut ($C_{average}$ = 12.9, very wide dispersion) and tallow potassium soap blends, considerable nonlinearity is found. Blends of maleic anhydride modified tallow and tallow soaps, and of maleinized soya and soya soaps show even greater nonlinearity than coco/tallow. A 40/60 soap solids ratio of maleinized soya soap and soya soap, each initially at 100 centipoise viscosity, yields a 5 centipoise solution. The striking thing here is that the overall chain length is unchanged. A measure of polydispersity by shape factors and more polarity has been introduced. This increased polydispersity can be accomplished much more economically using maleic modification of fatty acids than by using coco fatty acids and the emollency problems associated with short chain soaps can thus be avoided. The tendency to form liquid crystals is sharply reduced when a maleinized soap is present in a soap admixture.

It is apparent that the higher percentage solubility of high saponification number soaps is being inflated by the high inorganic content of the soap. This serves to obscure the true comparative solubilities of the organic fractions. Thus two soaps with different saponification numbers might show different soap solubilities when actually the concentration of organic material dissolved is the same. This could be important in uses in which the actual amount of fatty acids present is the critical factor. To clarify this, a plot of saponification numbers versus the fatty acid content of potassium soaps at the same soap viscosity was contended. Forty centipoises was chosen as a point of comparison to avoid the "break" noted in a number of soap solubility curves. It should be noted however, that considerably higher fatty acid content soaps can be prepared without loss in utility especially with the modified varieties.

There are apparently two families of solubility curves. Each increase rapidly in fatty acid solubility from the normal 15 to 17 percent as the saponification number rises to about 210 to 250. Afater this point, the rate of solubility increase is very slow with increasing saponification number and appears to approach asymptotically a limiting solubility which depends on the method of obtaining the increased saponification number. The polycarboxylic acid soaps of this invention have saponification numbers between 200 and 500, preferably 210 to 250. With coconut fatty acid blends (C = 12.9), the method is by reducing the average chain length and reaches 28.5 percent. When maleic modification is used, a distinct further increase in fatty acid solubility was obtained to more than twice the solubility of a monocarboxylic $C_{18}$ acids. These materials approached 35–36 percent solubility which surprisingly appears to be independent of the fatty acid blend maleinized. The difference can only be attributed to the shape factor contributed by the side chains introduced by the maleic addition reaction.

The advantages of this invention include among others, distinct improvements in fatty acid potassium soap solubility, lower viscosity, freedom from liquid crystal gels and modified fatty acid economically obtained after reaction of fatty acids with maleic anhydride when compared to intermixes of fatty acids and short chain fatty acids. At higher levels of modification the source of starting fatty acid made surprisingly little difference. A maleic modified fatty acid would be the material of choice when high solid soaps are desired.

The following examples are illustrative of the practice of this invention.

EXAMPLE 1

The maleinization procedure normally used during this work was as follows: Based on the fatty acid analysis of the oil or acid by GLC and the immediate objective the number of moles of maleic anhydride per mole monounsaturated and diunsaturated fatty acids was selected for that particular cook. This was varied considerably during the series depending on whether a theoretically full reaction was desired, or a certain fraction of full reaction, or whether a specific saponification number was desired. The grams of maleic per 100 grams oil or fatty acid was then calculated for that specific run. The maleic anhydride levels shown throughout this disclosure are on this "parts per 100 oil or acid" basis.

The cook ingredients are charged to give an 800 gram cook weight and heated electrically to 190° or 200°C. depending on the observed rate of exotherm and bubbling in the pot. The cook time was started at this point. This temperature was held for about 30 minutes until ebullition had diminished and then further heated to 220°C. This temperature was held for either two or four hours depending on the maleic anhydride charge and the extent of reaction desired.

Samples were drawn at one hour intervals for GLC analysis of the remaining fatty acids. In these, the sum of the saturated acids was used as an internal standard and the degree of fatty acid reaction calculated from this.

After the selected cook time had expired, the residual maleic anhydride was removed by steam sparging if the charge was a fatty aicd. If it was an oil (the glyceride), the reaction product was saponified with NaOH, reacidified, washed and dried under vacuum.

Several cooks with tall oil fatty acids and maleic anhydride were made, see Table 2. In the first, 51.5 parts maleic/100 of tall oil fatty acid was added. This is equivalent to 100 percent of the amount which could theoretically react assuming one mole reacting with the mono-unsaturated fatty acids and two moles reacting with the di-unsaturated acids. After cooking 3.5 hours at 225°C. and steam sparging, the saponification number was found to be 429 — well below the theoretical value of 512.

The results of viscosity and solubility for the modified fatty acids and oil are shown in Table 3. With regard to the maleic modified tall oil fatty acids no evidence of liquid crystal formation was noted although soap viscosities were rising rapidly at soap solids above about 43 percent. The rapid rise in viscosity began at 25 centipoises soap viscosity. Still, the viscosity was only 100 centipose at 49.6 percent solids (Cook No. 1) and higher solids solutions could have been prepared.

To illustrate the advantages of blending the modified fatty acids with its unmodified fatty acid a 50/50 mixture of tall oil fatty polycarboxylic acid from Cook No. 1 (in Table 2) was mixed with an unmodified tall oil fatty acid. As the results show in Table 3 the saponification number was reduced to 312. The solubility of the 50/50 mixture at 100 centipoise viscosity was only reduced to 47 percent; compared to 49.6 percent for Cook No. 1 and 20.6 percent for tall oil fatty acid soap alone at the same viscosity.

TABLE 2

CHARGE PROPORTIONS AND COOK CONDITIONS USED IN PREPARATION OF MALEINIZED FATTY ACIDS AND OILS

| Cook No. | Fatty Acid or Oil | Fatty Acid Sap No | Maleic Anhydride Parts/100 of Oil | Percent of Theory | Theoretical Sap. No. | Cook Conditions To Reach °C | Min. | °C | Min. | Cook Sap. No. |
|---|---|---|---|---|---|---|---|---|---|---|
|  | Maleic Anhydride | 1129 | — | — | 1144 | — | — | — | — | — |
| 1 | Tall Oil Fatty Acid | 195 | 51.48 | 100 | 512 | 200 | 22 | 225 | 210 | 429 |
| 2 | Tall Oil Fatty Acid | 195 | 16.60 | 31.6 | 328 | 200 | 7 | 220 | 130 | 242 |
| 3 | Tall Oil Fatty Acid | 195 | 8.30 | 15.8 | 267 | 205 | 16 | 220 | 105 | 240 |
| 4 A | Tallow Fatty Acid | 204 | 18.14 | 100 | 346 | 220 | 60 | — | — | 319 |
| B |  |  |  |  |  |  |  | 230 | 180 | 311 |
| C |  |  |  |  |  | Sparged | 230 | 210 | 301 |  |
| 5 A | Tallow Fatty Acid | 204 | 4.16 | 22.9 | 241 | 200 | 60 | 0 | 0 | 240 |
| B |  |  |  |  |  |  |  | 220 | 60 | 238 |
| C |  |  |  |  |  |  |  | 220 | 120 | 236 |
| D |  |  |  |  |  | Sparged | 220 | 150 | 238 |  |
| 6 A | Soya Fatty Acid | 201 | 47.5 | 100 | 500 | 200 | 30 | 220 | 60 | 429 |
| B |  |  |  |  |  |  |  | 220 | 180 | 410 |
| C |  |  |  |  |  |  |  | 220 | 270 | 391 |
| 7 A | Soya Fatty Acid | 201 | 32.5 | 68.5 | 429 | 200 | 30 | 220 | 150 | 354 |
| B |  |  |  |  |  | Sparged | 220 | 180 | 348 |  |
| 8 A | Corn Oil | — | 47.83 | 100 | 491 | 200 | 30 | 220 | 180 | 400 |
| B |  |  |  |  |  | Sparged | 220 | 210 | 342 |  |
| 9 | Linseed Oil | — | 54.07 | 74.1 | 536 | 200 | 60 | 220 | 150 | 394 |
| 10 | Tung Oil | — | 61.08 | 68.6 | 563 | 190 | 25 | 200 | 100 | 354 |

EXAMPLE 2

There are certain situations in which maleic modification of the naturally occurring fatty oil is preferable. Where a modified tallow fatty acid potassium soap is to be used and glycerine present would not interfere with the utility, or would be beneficial, it might be preferred to react maleic anhydride with tallow and saponify the glyceride afterward to yield the soap to be used. Similarly, where the fatty acids from an oil such as linseed or tung are so reactive and easily oxidized, maleinization of the oil may be the most practical way to get the modified product. After maleinization, the modified fatty acids should be much more stable to oxidation and heat polymerization. If necessary, the modified fatty acids could safely be recovered after maleic reaction, saponification and reacidification or alternatively by hydrolysis splitting.

The oils chosen for this demonstration from the large number of commercially available oils were corn oil, tung oil and linseed oil. The fatty acid composition of the oil was assumed to be that shown in Table 1. The corn oil analysis was actually run by GLC analysis of the recovered fatty acids. Because of the unstable nature of the linseed and tung oil acids, recorded fatty acid compositions were used. The maleic anhydride levels and cook schedules used are shown in Table 2, Cook Nos. 8–10. The polycarboxylic acids from each were recovered from the modified oil by saponification, reacidification and washing to remove the glycerine present. The oils were then dried under vacuum.

The potassium soaps of the recovered polycarboxylic acids showed excellent high solubility characteristics as shown in Table 3. The maleic anhydride treated linseed oil gave the highest potassium soap solubility noted to date (51 percent at 100 centipoise). Moreover, it was not treated with the maleic at the maximum theoretical reactivity level. Only two moles of maleic anhydride per mole of linolenic were added; whereas three moles should theoretically react.

EXAMPLE 3

Soya fatty acid was maleinized in two cooks at different maleic anhydride levels. Cook No. 7 in Table 2, made with 32.5 parts maleic/100 parts fatty acids, had a sap number of 347 after steam stripping. The solubility of this cook was evaluated as potassium soap alone and in admixture with unmodified soya soap to determine the effect that lower maleization levels or dilution with soya fatty acids would have on the viscosity of the soap. The viscosity/solids results shown in Table 3 indicate that remarkably little solubility was lost when 50% soya soap was blended with a soap from Cook No. 7.

TABLE 3

POTASSIUM SOAP AND FATTY ACID SOLUBILITY RESUME AT 40 AND 100 CPS.

VISCOSITY FOR THE VARIOUS OILS, FATTY ACIDS AND BLENDS EVALUATED

| Soap Blend Components Modified Fatty Acid or Oil | A % Maleic | Cook No. | B | A/B Soap Weight Ratio | Fatty Acid Blend Sap. No. | Solubility, Weight % 40 cps. % Soap | % Fatty Acid | 100 cps. % Soap | % Fatty Acid |
|---|---|---|---|---|---|---|---|---|---|
| Tall Oil Fatty Acid | 51.5 | 1 | tall oil fatty acid | 100/0 | 429 | 45.5 | 35.2 | 49.6 | 39.1 |
|  |  |  |  | 50/50 | 312 | 42.2 | 34.8 | 46.8 | 38.6 |
|  |  |  |  | 0/100 | 195 | 19.4 | 17.1 | 20.6 | 18.2 |
|  | 16.6 | 2 |  | 100/0 | 242 | 39.8 | 34.2 | 43.6 | 37.4 |
|  | 8.3 | 3 |  | 100/0 | 240.1 | 39.6 | 34.0 | 44.3 | 38.1 |
|  |  |  |  | 50/50 | 217.6 | 36.1 | 31.5 | 40.2 | 35.0 |
|  | 18.1 | 4 C | Tallow Fatty Acid | 100/0 | 300.6 | 41.8 | 34.7 | 44.9 | 37.3 |
| Tallow Fatty Acid |  |  |  | 25/75 | 227.9 | 33.0 | 28.6 | 37.0 | 32.0 |
|  |  |  |  | 13/87 | 216.4 | 25.7 | 22.4 | 29.0 | 25.3 |
|  |  |  |  | 0/100 | 203.7 | 19.3 | 17.0 | 20.5 | 18.0 |
|  | 4.16 | 5 B |  | 100/0 | 237.5 | 30.1 | 25.9 | 34.3 | 29.5 |
| Soya Fatty Acid | 47.5 | 6 C | Soya Fatty Acid | 100/0 | 390.8 | 41.0 | 32.4 | 45.1 | 35.6 |
|  | 32.5 | 7 B |  | 100/0 | 347.6 | 43.0 | 34.8 | 46.6 | 37.7 |
|  |  |  |  | 50/50 | — | 46.7 | — | 42.0 | — |
|  |  |  |  | 10/90 | 215.8 | 21.9 | 19.1 | 29.6 | 25.8 |
| Corn Oil | 47.8 | 8 |  | 100 | 342.5 | 36.6 | 29.7 | 39.7 | 32.2 |

TABLE 3-continued

POTASSIUM SOAP AND FATTY ACID SOLUBILITY RESUME AT 40 AND 100 CPS VISCOSITY FOR THE VARIOUS OILS, FATTY ACIDS AND BLENDS EVALUATED

| Soap Blend Components | | | A/B Soap | Fatty Acid | Solubility, Weight % | | | |
|---|---|---|---|---|---|---|---|---|
| Modified | A | | B Weight | Blend | 40 cps. | | 100 cps. | |
| Fatty Acid or Oil | % Maleic | Cook No. | Ratio | Sap. No. | % Soap | % Fatty Acid | % Soap | % Fatty Acid |
| Linseed Oil | 54.1 | 9 | 100 | 394.3 | 46.1 | 36.4 | 51.9 | 40.2 |
| Tung Oil | 61.1 | 10 | 100 | 354.4 | 44.7 | 36.0 | 50.2 | 40.5 |

EXAMPLE 4

Tallow fatty acids are much more highly saturated than either soya or tall oil fatty acids. Only about 3% is diunsaturated linoleic with the rest about evenly divided between saturated acids and monounsaturated acids. The Diels-Alder addition of maleic anhydride would be practically non-existent and, because of the low potential for reactivity, would not be a logical choice for maleic reaction. Amazingly, tallow fatty acids responded well to maleinizing and very high potassium soap solubilities resulted. The tallow fatty acid used contained 47.5% saturated fatty acids, 49.2% monounsaturated and only 3.3% linoleic as shown in Table 1. Two cooks, Cooks 4–5 in Table 2, were made, one with 18.1 parts maleic and the other with 4.2 parts maleic per 100 parts of fatty acid. These gave 45 and 34 percent soap solubility at 100 centipoise, respectively, compared to 20.5% for the untreated tallow fatty acids.

In one series designed to demonstrate an area of utility of the modified tallow fatty acids, it was decided to duplicate the potassium soap solubility of coco soap and commercially important coco/tallow blends with maleinized tallow/tallow blends. A GLC analysis of Ivory soap fatty acids indicated that it approached the 75/25 tallow/coco ratio. The potassium soap solubility of coconut fatty acids was duplicated by a 75 tallow/25 Cook No. 4 ratio.

From the foregoing illustrations it becomes obvious that, if potassium soap solubility is the primary requirement of a product which now requires coco fatty acids, this same solubility can be obtained by combination of an almost infinite variety of fatty acids, maleic or acrylic modification levels, or blends of modified or unmodified fatty acids. If the saturated character of the coco acids iss also important, very cheap tallow fatty acids can be modified with maleic anhydride cheaply and approach these characteristics in most respects.

While the invention has been described and illustrated herein by references to various specific materials, procedures and examples, it is understood that the invention is not restricted to the particular materials, combinations of materials, and procedures selected for that purpose. Numerous variations of such details can be employed, as will be appreciated by those skilled in the art.

Having thus described the invention, what is claimed is;

1. A soap composition consisting essentially of,
   a. from 10 to 90 percent by weight of a polycarboxylic acid soap consisting of a fatty acid or oil from the group consisting essentially of soya fatty acid, tall oil fatty acid, cotton seed fatty acid, tallow fatty acid, corn oil, tung oil and linseed oil modified by reacting with a maleyl compound from the group consisting essentially of maleic anhydride and maleic acid at a temperature between 180°C. and 300°C. for between 30 minutes and 6 hours and neutralized with a member of the group consisting essentially of potassium, sodium and ammonium, and
   b. 10 to 90 percent by weight of a soap from the group consisting essentially of tall oil fatty acid, oleic acid, tallow, coconut fatty acids and soya fatty acid.

* * * * *

UNITED STATES PATENT OFFICE
CERTIFICATE OF CORRECTION

PATENT NO. : 3,933,780
DATED : January 20, 1976
INVENTOR(S) : Benjamin F. Ward

It is certified that error appears in the above-identified patent and that said Letters Patent are hereby corrected as shown below:

Column 3, line 63, "aicd" should read --acid--.

Column 6, line 37, "aicd" should read --acid--.

In Table 2, columns 7 and 8, Cook Nos. 4C, 5D, 7B and 8B should read as follows:

TABLE 2

CHARGE PROPORTIONS AND COOK CONDITIONS USED IN PREPARATION OF MALEINIZED FATTY ACIDS AND OILS

| Cook No. | Fatty Acid or Oil | Fatty Acid Sap. No. | Maleic Anhydride Parts/100 of Oil | Percent of Theory | Theoretical Sap. No. |
|---|---|---|---|---|---|
| 4 A | Tallow Fatty Acid | 204 | 18.14 | 100 | 346 |
| B | | | | | |
| C | | | | | |
| 5 A | Tallow Fatty Acid | 204 | 4.16 | 22.9 | 241 |
| B | | | | | |
| C | | | | | |
| D | | | | | |
| 6 A | Soya Fatty Acid | 201 | 47.5 | 100 | 500 |
| B | | | | | |
| C | | | | | |
| 7 A | Soya Fatty Acid | 201 | 32.5 | 68.5 | 429 |
| B | | | | | |
| 8 A | Corn Oil | -- | 47.83 | 100 | 491 |
| B | | | | | |

UNITED STATES PATENT OFFICE
CERTIFICATE OF CORRECTION

PATENT NO. : 3,933,780
DATED : January 20, 1976
INVENTOR(S) : Benjamin F. Ward

It is certified that error appears in the above—identified patent and that said Letters Patent are hereby corrected as shown below:

TABLE 2 (continued)

CHARGE PROPORTIONS AND COOK CONDITIONS USED IN PREPARATION OF MALEINIZED FATTY ACIDS AND OILS

| Cook Conditions | | | | Cook Sap. No. |
|---|---|---|---|---|
| To Reach °C | Min. | °C | Min. | |
| 220 | 60 | -- | -- | 319 |
|  |  | 230 | 180 | 311 |
| Sparged |  | 230 | 210 | 301 |
| 200 | 60 | 0 | 0 | 240 |
|  |  | 220 | 60 | 238 |
|  |  | 220 | 120 | 236 |
| Sparged |  | 220 | 150 | 238 |
| 200 | 30 | 220 | 60 | 429 |
|  |  | 220 | 180 | 410 |
|  |  | 220 | 270 | 391 |
| 200 | 30 | 220 | 150 | 354 |
| Sparged |  | 220 | 180 | 348 |
| 200 | 30 | 220 | 180 | 400 |
| Sparged |  | 220 | 210 | 342 |

Column 10, line 15, "iss" should read --is--.

Signed and Sealed this first Day of June 1976

[SEAL]

Attest:

RUTH C. MASON
Attesting Officer

C. MARSHALL DANN
Commissioner of Patents and Trademarks